US00PP27929P2

(12) United States Plant Patent
Nobles

(10) Patent No.: US PP27,929 P2
(45) Date of Patent: Apr. 25, 2017

(54) ***FICUS* PLANT NAMED 'LITTLE MISS FIGGY'**

(50) Latin Name: *Ficus carica*
Varietal Denomination: Little Miss Figgy

(71) Applicant: Michael Nobles, Ridgeville, SC (US)

(72) Inventor: Michael Nobles, Ridgeville, SC (US)

( * ) Notice: Subject to any disclaimer, the term of this patent is extended or adjusted under 35 U.S.C. 154(b) by 74 days.

(21) Appl. No.: 14/545,540

(22) Filed: May 18, 2015

(51) Int. Cl.
*A01H 5/08* (2006.01)

(52) U.S. Cl.
USPC ..... Plt./211

(58) Field of Classification Search
USPC ..... Plt./211
See application file for complete search history.

*Primary Examiner* — Anne Grunberg
(74) *Attorney, Agent, or Firm* — Penny J. Aguirre

(57) ABSTRACT

A new cultivar of *Ficus carica* plant named, 'Little Miss Figgy', that is characterized by its compact, dwarf plant habit, its prolific production of large fruit that is present along the branches, its leaves that are deeply lobed and dark green in color, and its very short internode lengths between lateral branches.

2 Drawing Sheets

Botanical classification: *Ficus carica.*
Variety denomination: 'Little Miss Figgy'.

BACKGROUND OF THE INVENTION

The present invention relates to a new and distinct cultivar of *Ficus carica*. The new *Ficus* will hereafter be referred to by its cultivar name, 'Little Miss Figgy'. 'Little Miss Figgy' is a new cultivar of deciduous shrub grown for use as an ornamental and fruit bearing plant for the landscape.

The Inventor discovered the new cultivar in September of 2010 as a naturally occurring branch mutation of *Ficus* 'Violette de Bordeaux' (not patented) in a container at his nursery in Ridgeville S.C., USA.

Asexual propagation of the new cultivar was first accomplished by tissue culture under the direction of the Inventor in January of 2014 in Eustis, Fla. Asexual propagation by tissue culture and stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Little Miss Figgy' as a unique cultivar of *Ficus.*

1. 'Little Miss Figgy' exhibits a compact, dwarf plant habit.
2. 'Little Miss Figgy' exhibits prolific production of large fruit that is present along the branches.
3. 'Little Miss Figgy' exhibits leaves that are deeply lobed and dark green in color.
4. 'Little Miss Figgy' exhibits very short internodes between lateral branches.

'Violette de Bordeaux', the parent of 'Little Miss Figgy', differs from 'Little Miss Figgy' in having a much larger plant size, in producing fewer fruits that are smaller in size, and in having longer branch internode lengths. 'Little Miss Figgy' can be most closely compared to the *Ficus* cultivars 'Black Mission' (not patented) and 'Chicago Hardy' (not patented). 'Black Mission' is similar to 'Little Miss Figgy' in having fruit that is deep burgundy in color and in having fruit with a sweet strawberry type center. 'Black Mission' differs from 'Little Miss Figgy' in having a much larger plant size, in producing much fewer fruits that are borne at the ends of branches, and in being less cold hardy. 'Chicago Hardy' is similar to 'Little Miss Figgy' in producing large quantities of fruit that are deep burgundy in color and in having a spring and fall fruiting season. 'Chicago Hardy' differs from 'Little Miss Figgy' in being much larger in size, in having leaves with lobes that are more rounded in shape, in being more easily propagated, and in producing fruits at the ends of branches.

BRIEF DESCRIPTION OF THE DRAWINGS

The accompanying colored photographs illustrate the overall appearance and distinct characteristics of the new cultivar. The plant in the photographs is about one year in age as grown outdoors in a 3-gallon container in Ridgeville, S.C.

The photograph in FIG. 1 provides a side view of the plant habit of 'Little Miss Figgy'.

Figure 1:
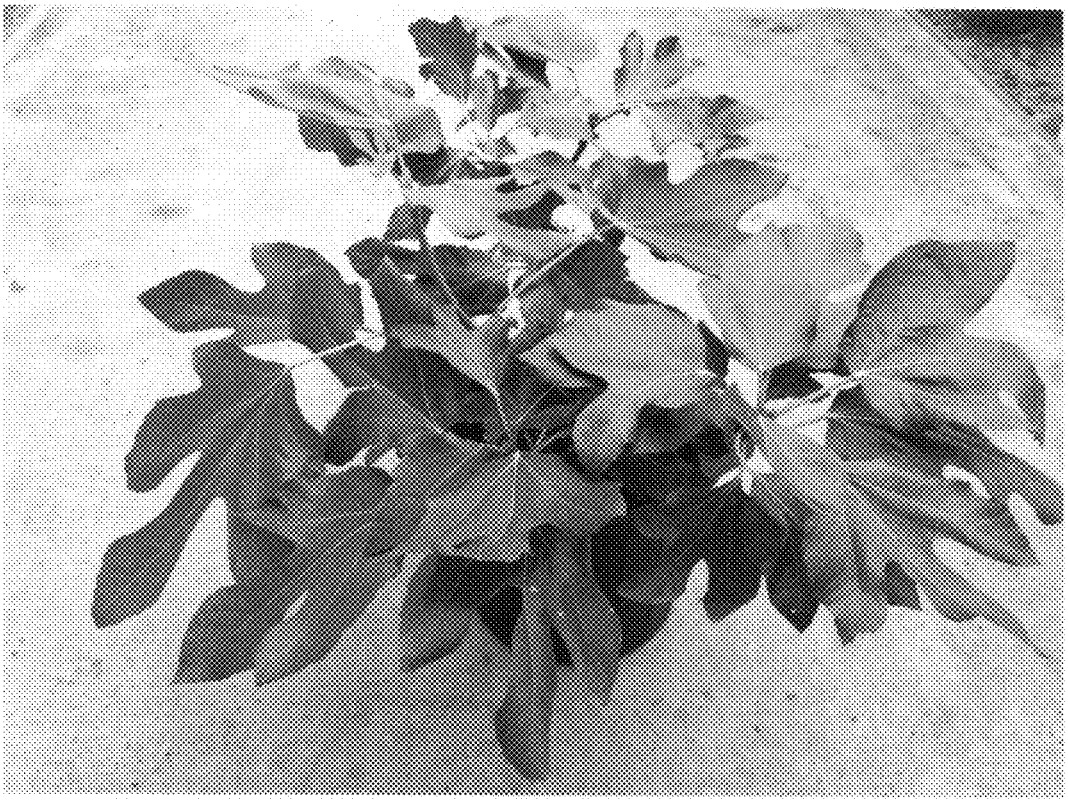
Figure 2:
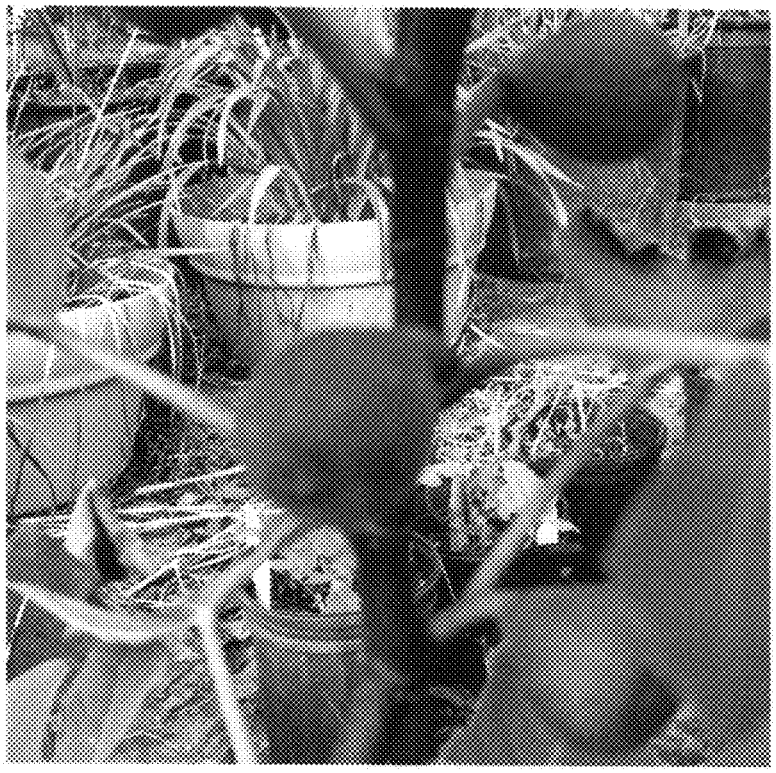

The photograph in FIG. 2 provides a close-up view of the fruit of 'Little Miss Figgy'.

Figure 3:
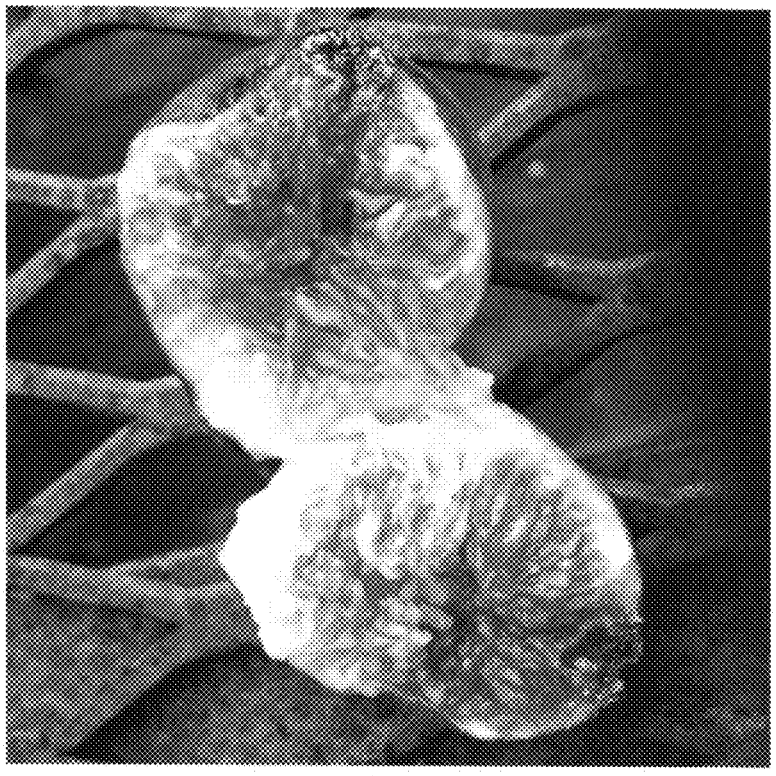

The photograph in FIG. 3 provides a close-up view of the interior of the infructescence of 'Little Miss Figgy'.

The colors in the photographs are as close as possible with the digital photography techniques available, the color values cited in the detailed botanical description accurately describe the colors of the new *Ficus*

DETAILED BOTANICAL DESCRIPTION

The following is a detailed description of one year old plants of the new cultivar as grown outdoors in 3-gallon containers in Ridgeville, S.C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Plant type*.—Perennial shrub.

*Plant habit*.—Compact, dwarf, upright.

*Plant size*.—Reaches about 0.91 m in height and spread.

*Cold hardiness*.—At least in U.S.D.A. Zones 7.

*Diseases and pests*.—Similar susceptibility and resistance to diseases and pests as other *Ficus* cultivars has been observed.

*Root description*.—Fine and fibrous.

*Propagation*.—Tissue culture (preferred) and stem cuttings.

*Growth rate*.—Moderate.

Stem description:

*Shape*.—Rounded.

*Stem color*.—Young branches; 145A, slightly tinged 174A and becoming suffused with 200C, mature branches; 200A to 200C.

*Stem size*.—An average of 45 cm in length and 6 mm in diameter.

*Stem surface*.—Smooth and slightly puberulent.

*Stem strength*.—Moderately strong and flexible.

*Branching*.—An average of 10 lateral branches, plant does not form suckers or bark tubers.

*Branch internode length*.—An average of 4 cm.

Foliage description:

*Leaf shape*.—Ovate.

*Leaf division*.—Single.

*Leaf base*.—Rounded to truncate.

*Leaf apex*.—Acute.

*Leaf venation*.—Pinnate, 154A to 154C in color on upper and lower surface.

*Leaf margins*.—3 to 5 lobed, deeply lobed with lobes primarily oblanceolate to elliptic in shape.

*Leaf arrangement*.—Alternate.

*Leaf attachment*.—Petiolate.

*Leaf surface*.—Both surfaces scaberlulose.

*Leaf fragrance*.—Slight sweet fig scent.

*Leaf size*.—An average of 15 cm in length and 12 cm in width.

*Leaf quantity*.—An average of 4 per branch 45 cm in length.

*Leaf color*.—New growth upper surface; 138A, new growth lower surface; 138B, mature growth upper and lower surface 137B.

*Petioles*.—An average of 7 cm in length and 2 mm in width and 145C to 145D in color, scaberlulose surface, rounded in shape.

Flower description:

*Blooming period*.—Flowers develop internally in fruit as an infructescence, which are present in the spring from April to mid-June and again in the fall from early September to early November in South Carolina with fruit about 8 to 10% smaller in the fall.

*Inflorescence type*.—Syconium, flowers borne internally on a hollow inverted receptacle, which is lined with numerous unisexual flowers, the flower itself is not visible outwardly, as it blooms inside the infructescence.

*Lastingness of inflorescence*.—Not applicable, develops in fruit.

*Flower number*.—Numerous unisexual flowers per infructescence.

*Peduncle* (*fruit stalk*).—Round in shape, held outward from the main stem, an average of 2.5 cm in length and 2 mm in width, 145C to 145D in color, scaberlulose surface, easily abscisses from twig.

*Reproductive organs*.—To minute to observe, senesce as fruit matures.

*Infructescence*.—Present at axils of leaf nodes of branches, obovate in shape, an average of 4 cm in length and 5 cm in diameter, rounded apex, fruit neck is absent, ostiole; an average of 1.3 mm in width, drop at the eye is absent ostiole scales; adhered, an average of 1.3 mm in length and 2.4 mm in width, and 183C in color, resistant to ostiole end cracks, skin; medium firm and satiny, moderately lenticillate with lenticels 0.7 mm in length and 163A to 163D in color, bloom, longitudinal ribs, and skin cracks are absent, skin is difficult to peel adhering to about 95% or more of meat, fruit size and formation is uniform, outer surface color; 138A, heavily suffused with irregular patches a blend of 163C and 70A, inner surface; interior a blend of N34C and 184A to 184C and a thin layer of 157A on edges, fruit flesh is an average of 3.3 cm in thickness at the center, pulp; fine texture, neutral flavor, 184D in color, doughy, fruit cavity; 3.8 cm in length and width, fruitlets; not observed, seeds: numerous, minute, and 162B in color.

It is claimed:

1. A new and distinct cultivar of *Ficus* plant named 'Little Miss Figgy' as herein illustrated and described.

* * * * *